United States Patent [19]

Dang Vu et al.

[11] Patent Number: 5,030,789

[45] Date of Patent: * Jul. 9, 1991

[54] CATALYTIC METHOD FOR THE DIMERIZATION, CODIMERIZATION OR OLIGOMERIZATION OF OLEFINS WITH THE USE OF AN AUTOGENOUS THERMOREGULATION FLUID

[75] Inventors: Quang Dang Vu, Neuilly; Yves Chauvin, Le Pecq, both of France

[73] Assignee: Institut Francais du Petrole, Rueil Malmaison, France

[ * ] Notice: The portion of the term of this patent subsequent to Jul. 24, 2007 has been disclaimed.

[21] Appl. No.: 371,777

[22] Filed: Jun. 27, 1989

[30] Foreign Application Priority Data

Jun. 28, 1988 [FR] France ............................... 88 08799

[51] Int. Cl.$^5$ .......................... C07C 2/00; C07C 2/04
[52] U.S. Cl. .................................... 585/503; 585/510; 585/910; 585/911; 585/921; 585/922; 585/924; 585/925; 585/926; 422/200
[58] Field of Search ............... 585/503, 510, 910, 911, 585/924, 922, 925, 926; 422/200

[56] References Cited

U.S. PATENT DOCUMENTS 4,709,111 11/1987 Ward .................................. 585/503
4,943,669 7/1990 Dang Vu et al. ................... 585/503

*Primary Examiner*—W. J. Shine
*Assistant Examiner*—Douglas J. McGinty
*Attorney, Agent, or Firm*—Millen, White & Zelano

[57] ABSTRACT

The invention provides a catalytic method for the dimerization or codimerization or oligomerization, in particular selective, of olefins, carried out under pressure, in a reaction zone 1 containing a solid catalyst bed in which is disposed a plurality of hollow internal spaces 6.3a defined by walls, each being divided into an upper semi-space 6.3, 1a and a lower semi-space 6.3, 2a which communicate together through a connecting zone 6.6a. An autogenous thermoregulation fluid flows, in the form of a sheet, in said hollow internal spaces 6.3a after passing through a central distributing zone 6.1a and distributing zones 6.2a and before passing into collecting zone 6.4a and into a central collecting zone 6.5a.

15 Claims, 3 Drawing Sheets

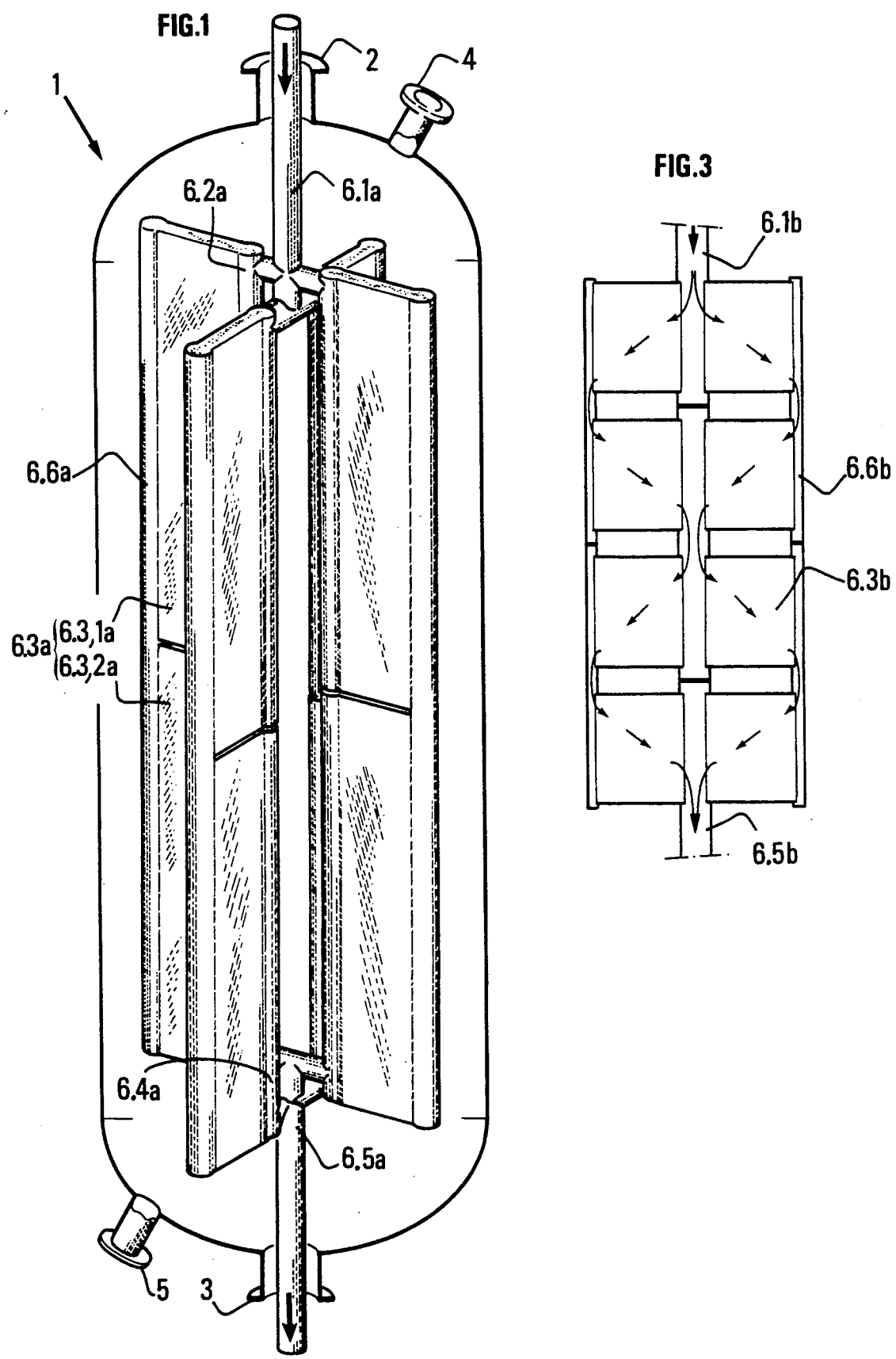

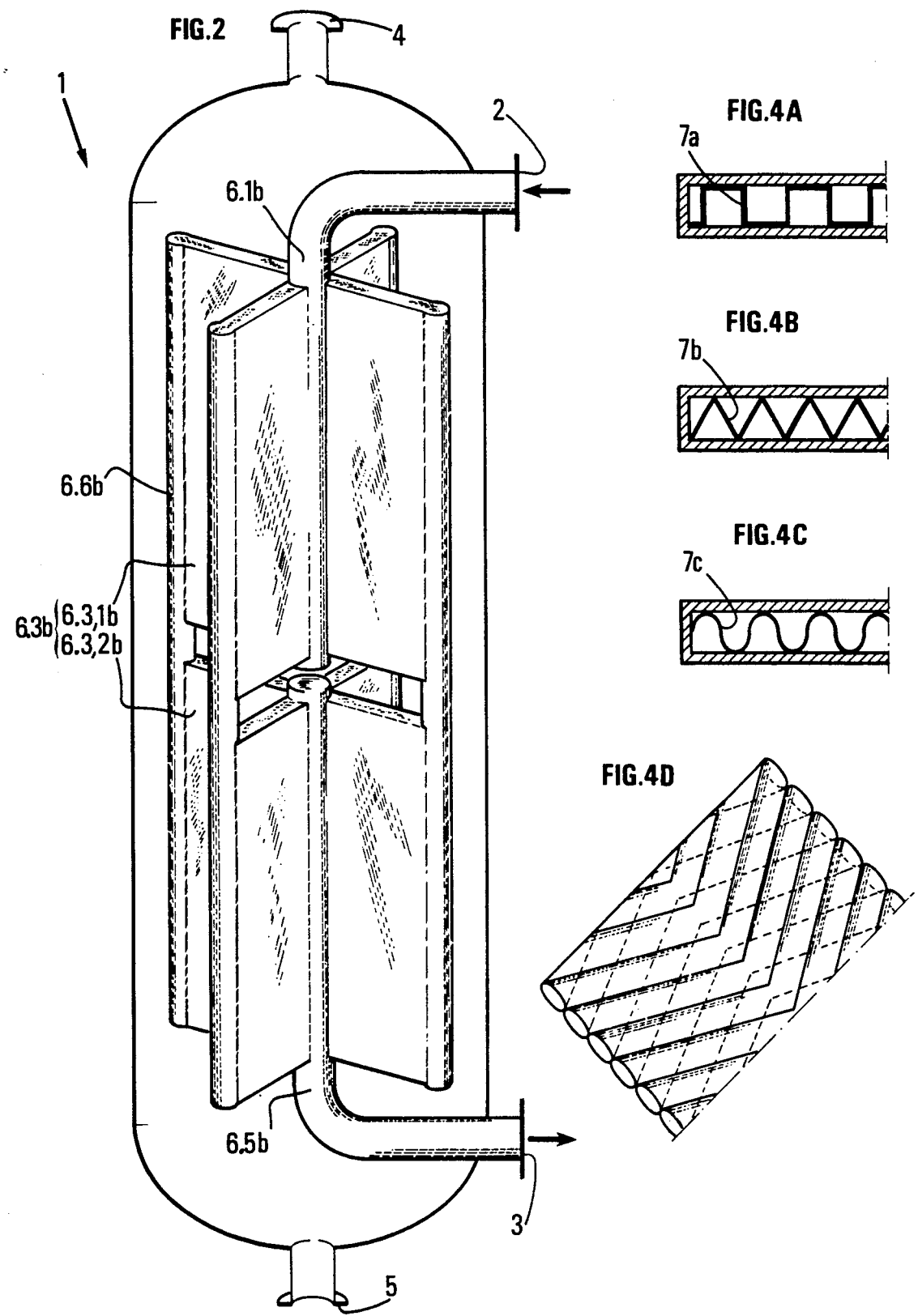

CATALYTIC METHOD FOR THE DIMERIZATION, CODIMERIZATION OR OLIGOMERIZATION OF OLEFINS WITH THE USE OF AN AUTOGENOUS THERMOREGULATION FLUID

BACKGROUND OF THE INVENTION

1. Field of the Invention

The invention relates to a method for carrying out, generally under pressure, the (notably selective) dimerization, codimerization and oligomerization reactions of olefins in the presence of at least one catalyst, usually solid, in at least one reaction zone whose temperature is controlled by a heat-exchange device with hollow plates disposed therein.

Generally, in this type of reactions, when operating in accordance with the invention, at least one of the reagents is either in the liquid state, or in a state making circulation thereof by means of a pump possible (supercritical state), such that the ratio Tr between the temperature T (in Kelvin degrees) of the reagent system and the (pseudo-) critical temperature Tc (in Kelvin degrees) of said system is preferably less than 2, for example than 1.5.

The olefin used may more particularly be chosen from ethylene, propylene, styrene, one of the isomers of the butenes or one of the mixtures thereof. This olefin may be used in the pure state or mixed with one or more compounds not reacting on the catalyst in the conditions used, such for example as cyclic or acyclic saturated hydrocarbons, in particular those having from 2 to 10 carbon atoms. The olefin concentration in the mixture may be from 5 to 100%, preferably from 10 to 100% by weight.

The invention relates more particularly to a method for the selective dimerization of propylene into methyl-4 pentene-1, for example by means of solid potassium and/or sodium based catalysts.

2. Description of the Prior Art

It is known to dimerize or oligomerize olefins in the homogeneous liquid phase so as to obtain, for example, C6 dimates (patents belonging to the Applicant U.S. Pat. No. 4,283,305 and U.S. Pat. No. 4,366,087).

It is much more difficult to carry out selective dimerization when using a heterogeneous catalyst, for example for dimerizing propylene into methyl-4 pentene-1, with sufficient selectivity, particularly greater than 85%. It is in fact then necessary to maintain a relatively constant temperature, within fairly narrow limits, below which the activity of the catalysts drops to a value which makes the reaction industrially unusable and above which consecutive isomerization reactions take place, lower the selectivity and cause practically insurmountable separation problems.

The isotherm reaction system the most often used is the single pass calender tube reactor where the inside of the tubes is filled with catalyst and thus forms the reaction medium. But, in selective dimerization, the catalytic system generally undergoes spontaneous and/or accidental (due to impurities) de-activation, which requires the periodic renewal of this catalyst, a constraint which is technically difficult to put into practice with a reactor in which the high number of tubes must be filled and emptied one by one manually.

It is also known, when the temperature of the reaction is to be maintained within relatively narrow limits to place in the catalyst bed a heat transfer apparatus either tube-based (GB No. 2,046,618), or plate-based (U.S. Pat. No. 3,666,423) or grid-based (U.S. Pat. No. 4,693,807), and to cause a fluid to flow inside this apparatus for providing heat transfer and commonly designated under the name of thermoregulation fluid.

The drawback in the use of a tube-based heat transfer apparatus is due to the fact that the connection between these individual tubes is very cumbersome and, consequently, it is very difficult to fit the assembly correctly inside the reactor. The drawback of the plate based heat transfer apparatus of U.S. Pat. No. 3,666,423 is its bulk and its low efficiency. In order to withstand the reaction pressure, the plates are only partially hollow and the thermoregulation fluid thus has only a small portion of the area of the plates for carrying out its exchange work.

In his U.S. Pat. No. 4,544,544, there has been proposed, for gas reagent systems, a method for using hollow plates, made from thin metal sheets and with rectangular internal section.

The plates used in the method of the present invention work very little under stress, which makes it possible to hollow them out completely and to let the thermoregulation fluid provide the exchange through the whole of the available area. In addition, fitting and connections are sufficiently simple so as to be readily carried out in the restricted space offered by the reactor.

SUMMARY OF THE INVENTION

The present invention uses a continuous single-stage reaction system equipped with a heat transfer apparatus comprising plates (or hollow internal spaces). FIGS. 1, 2 and 3 illustrate the path of the thermoregulation fluid through said hollow internal spaces and FIG. 5 explains the operation of the unit:

the reaction fluid will first of all be used as thermoregulation fluid for the unit and the catalyst bed; then it will flow through the solid catalyst bed enclosed in an envelope 1 substantially cylindrical and elongate in shape;

The inside of the catalyst bed is cooled by the flow of thermoregulation fluid which flows through a heat exchange device disposed in said catalytic bed and comprising hollow plates manufactured, for example, from thin flat or corrugated metal sheets as will be explained further on;

the thermoregulation fluid flowing inside the plates comprises the reagent(s) forming the fresh charge, the flow of this fluid being usually provided by at least one pump 13;

the thermoregulation system is a system open on the reaction system; in fact, it is continuously fed by the make-up reagent(s) which pass directly from the thermoregulation system into the reactor without any permanent or transitory mechanical barrier.

According to the method of the invention, the fresh charge (e.g. liquid propylene) is fed, under a pressure generally between 1.2 and 12 MPa, into the duct 8 of the manufacturing unit (manufacturing for example methyl-4 pentene-1).

This fresh charge is first of all preferably preheated indirectly by the hot reaction effluent (coming from duct 5) through the heat exchanger 9. It then passes into duct 10 and meets a recycled fraction of the thermoregulation fluid which will be called "recycled charge"

hereafter this recycled fraction being conveyed by duct 11.

The weight ratio between the recycled charge and the fresh charge is usefully between 1 and 500, preferably between 2 and 200 and even more preferably between 5 and 100.

The mixture thus obtained (fresh charge plus recycled charge) forms the thermoregulation fluid (or heat-carrying fluid) of the reactor 1. This fluid, which is generally between 100° and 200° C., preferably about 150° C., and at a temperature reduced by about 1.13, and in a state such that it may still be conveyed by a pump, penetrates into duct 2 inside the hollow coolant plates 6.3a or 6.3b disposed within the catalyst bed contained in the reactor 1.

The thermoregulation fluid absorbs the reaction heat released as the product of synthesis is formed (e.g. methyl-4 pentene-1 obtained by selective dimerization of propylene). This fluid leaves reactor 1 through duct 3.

It is then separated into two portions. A first portion forms the charge to be processed which will flow through the catalyst bed. This charge will hereafter be called "make-up charge". It is fed to reactor 1 through duct 14. A second portion of the thermoregulation fluid drawn off through duct 3 will be recycled through duct 11 into the heat exchange plates 6.3a or 6.3b (mixed with some fresh charge from duct 10). This second portion of thermoregulation fluid is called "recycled charge".

The "recycled charge" passes through duct 12 where it is drawn in by pump 13 (preferably centrifugal) to be injected into duct 11 already mentioned.

In accordance with the characteristics of the invention, the weight ratio between the recycled charge and the make-up charge is advantageously between 1 and 500, preferably between 2 and 200 and even more preferably between 5 and 100. Too low a ratio prevents satisfactory heat control within the catalytic bed; too high a ratio requires a flow section such that the hollow plates become too thick and too cumbersome.

The "make-up charge", not taken up by the pump 13, passes into duct 14 through the exchanger 15 whose purpose is to re-adjust the temperature at the input to reactor 1 to the desired level. This make-up charge leaves exchanger 15 through duct 4 and then passes through the catalyst bed contained in reactor 1. The resultant reaction effluent is discharged from the reactor through duct 5 for preheating the fresh charge through exchanger 9. From 9, said effluent is usefully directed, through duct 16, to a distillation and conditioning unit (not shown in the figure).

When it is a question of dimerizing propylene selectively into methyl-4 pentene-1, an alkaline carbonate based catalyst for example is used preferably impregnated by the metal of the same family.

Because of the good heat control provided by the plate cooling system, it has been possible to push the conversion very far without the selectivity of the operation being affected thereby.

Thus, the invention has as object a catalytic method for dimerizing or codimerizing or oligomerizing olefins carried out usually under pressure, in the presence of a solid catalyst, in a reaction zone defined by a substantially cylindrical enclosure whose section is substantially circular, said enclosure containing a generally fixed catalyst bed in which a plurality of hollow internal spaces is disposed, through which flows a thermoregulation fluid, at a pressure substantially equal to the pressure to which the reaction mixture is subjected, in which method:

a fresh liquid charge (containing at least one olefin), mixed with a recycled charge defined below, is introduced into said hollow internal spaces defined by walls, the weight ratio between the recycled charge and the fresh charge being between 1 and 500, the fresh charge-recycled charge mixture forming the thermoregulation fluid;

the thermoregulation fluid is drawn off from said hollow internal spaces and this fluid is separated into two portions called hereafter recycled charge and make-up charge, the weight ratio between said recycled charge and said make-up charge being between 1 and 500;

said recycled charge is fed into said hollow internal spaces as thermoregulation fluid component;

said make-up charge is fed into said catalyst bed;

a reaction effluent is drawn off from said catalyst bed.

The method of the invention is further characterized by a particular travel path for the thermoregulation fluid (or heat-carrying fluid) through said hollow internal spaces.

BRIEF DESCRIPTION OF THE DRAWINGS

According to the invention, there are several ways of causing this fluid to flow along a path, illustrated in FIGS. 1, 2 and 3:

FIG. 1 corresponds to a first type of flow path for the thermoregulation fluid;

FIGS. 2 and 3 correspond to the second type of flow path for this fluid.

FIGS. 4A, 4B, 4C, and 4D show plates in accordance with different improvements of the invention.

DESCRIPTION OF THE PREFERRED EMBODIMENTS

Figure 5:
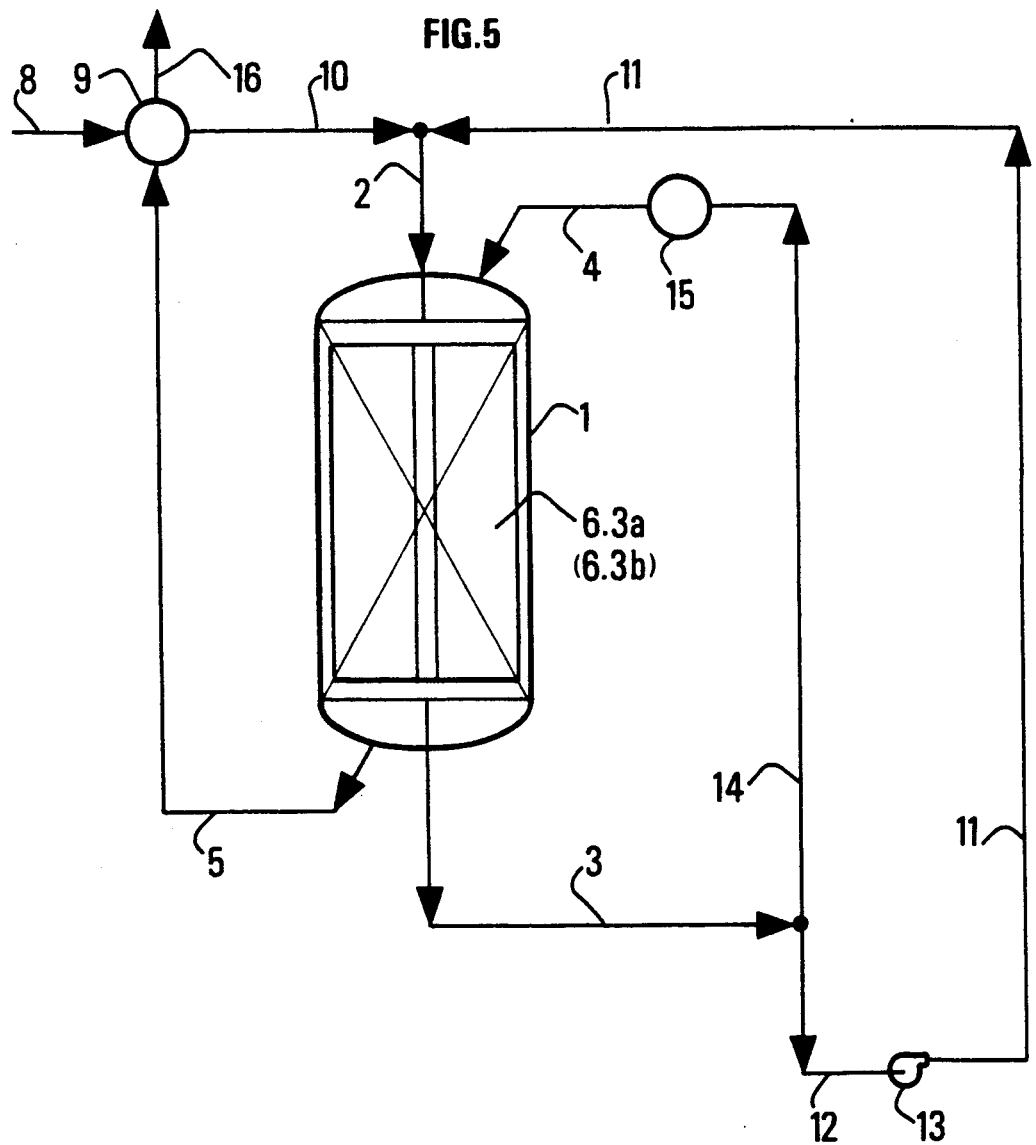
FIG. 5 is a schematic flow diagram of an overall process employing the invention, which is further described in Example 1.

In these figures, the plates (or hollow internal spaces) are shown as having flat faces. FIGS. 4A, 4B, 4C and 4D show plates in accordance with different improvements of the invention.

In the two types of flow path of the thermoregulation fluid, a reaction zone or enclosure is used, of a substantially cylindrical shape and whose section has a substantially circular shape, comprising at least one duct 2 for introducing said thermoregulation fluid, at least one duct 3 for drawing off said thermoregulation fluid, at least one duct 4 for introducing a so-called make-up charge into the reaction zone and at least one duct 5 for drawing off the reaction effluent from said reaction zone. The level of the intake duct 4 and the level of the outlet duct 5 may be arranged at any adequate position of the enclosure 1, for example as shown in FIGS. 1, 2 and 5.

The apparatus used in the first type of thermoregulation fluid flow further comprises (see FIG. 1):

(a) at least one central distributing collector 6.1a, for example vertical, whose axis corresponds generally to the axis of the enclosure 1, which is situated in the upper part of the enclosure and is connected to duct 2, (b) a plurality of distributing collectors 6.2a, parallel to the axis of the enclosure, these collectors being connected individually, towards their top, to the central distributing collector 6.1a, (c) at least one central receiving collector 6.5a, for example vertical, whose axis corresponds generally to the axis of the enclosure, which is situated in the lower part of the enclosure and is connected to duct 3, (d) a plurality of receiving collectors 6.4a, parallel to the axis of the enclosure, these collectors being, on the one hand, connected individually, towards their base, to the central receiving collector 6.5a, and, on the other hand, each situated in the extension of a corresponding distributing collector 6.2a, the contact surface between a receiving collector 6.4a and its corresponding distributing collector 6.2a being sealed, (e) a plurality of connecting collectors 6.6a, each of them being, on the one hand, parallel to the axis of the enclosure, to a distributing collector 6.2a and to the corresponding receiving collector 6.4a and on the other hand, situated in the same plane defined by this distributing collector 6.2a, this receiving collector 6.4a and the axis of the enclosure, (f) a plurality of hollow continuous and elongate plates (hollow internal spaces) 6.3a intended for the flow of the thermoregulation fluid, each plate being divided, in the width direction, into two hollow semi-panels or hollow internal semi-spaces 6.3, 1a and 6.3, 2a, the contact surface between these two semi-panels being sealed, these two semi-panels being open on to a connecting collector 6.6a which causes the two semi-panels 6.3, 1a and 6.3, 2a to communicate with each other, the upper semi-panel or upper semi-space 6.3, 1a being open on to a distributing collector 6.2a, the lower semi-panel or lower semi-space 6.3, 2a being open on to the corresponding receiving collector 6.4a.

According to an improvement, the faces of said hollow plates may be formed by corrugated metal sheets whose corrugations are chosen from one of the following forms: square, rectangular, triangular, sinusoidal and a herring bone pattern (see FIG. 4D), the aim being to create a high turbulence in the flow of the thermoregulation fluid.

In the apparatus used in the first type of thermoregulation fluid flow, said hollow plates are substantially parallelepipedic 6.3a, each plate comprising two wide parallel faces defining a plane disposed radially with respect to the axis of the enclosure 1 and four thin faces, two of them being parallel to the axis of the enclosure, the other two being perpendicular to this axis; each plate is divided, in the width direction, into two hollow semi-panels or hollow internal semi-spaces 6.3, 1a and 6.3, 2a, the contact surface between these two semi-panels being sealed. These two semi-panels are open, over the whole of their thin face parallel to the axis of the enclosure and the furthest away from the axis, on to a connecting collector 6.6a which causes the two semi-panels 6.3, 1a and 6.3, 2a to communicate with each other. The upper semi-panel or upper semi-space 6.3, 1a opens over the whole of its thin face parallel to the axis of the enclosure and the closest to this axis, on to the corresponding receiving collector 6.4a. Said thin faces of each hollow plate may possibly be not flat, but for example semi-cylindrical.

In FIG. 1, given by way of example, the path of the thermoregulation fluid through hollow plates (hollow internal spaces) which are substantially parallelepipedic (contained in the reaction zone) will be described:

the autogenous thermoregulation fluid formed by the component(s) constituting the fresh charge (and so the recycled charge) is fed into a central distributing zone 6.1a, said fluid from the central distributing zone 6.1a is divided up into distributing zones 6.2a, said fluid is fed, from said distributing zones 6.2a, into said upper hollow internal semi-spaces 6.3, 1a, defined by walls, each upper semi-space 6.3, 1a having a substantially parallelepipedic shape (each upper semi-space thus comprising two wide parallel faces defining a plane disposed radially with respect to the axis of the reaction zone 1 and four thin faces, two of which are parallel to the axis of the reaction zone 1 and the other two being perpendicular to this axis), said fluid penetrating into said upper semi-spaces 6.3, 1a through their thin face parallel to the axis of the reaction zone defined by a substantially cylindrical shaped enclosure 1, this face being the closest to this axis, said fluid is caused to flow inside said upper hollow internal semi-spaces 6.3, 1a in the form of a sheet, said fluid is discharged from said upper semi-spaces 6.3, 1a, through their thin face parallel to the axis of the reaction zone 1 and the furthest away from this axis, into connecting zones 6.6a which each connect an upper semi-spaces 6.3, 1a with a lower hollow internal semi-spaces 6.3, 2a situated in the extension of said upper semi-spaces 6.3, 1a, each lower semi-space 6.3, 2a being defined by walls and having a substantially parallelepipedic shape which is defined as for an upper semi-space 6.3, 1a, said fluid is caused to penetrate, from said connecting zones 6.6a, into said lower semi-space 6.3, 2a through their thin face parallel to the axis of the reaction zone 1 and the furthest from this axis, said fluid is caused to flow inside said lower hollow internal semi-spaces 6.3, 2a in the form of a sheet, said thermoregulation fluid is discharged from said lower semi-space 6.3, 2a, through their thin face parallel to the axis of the reaction zone 1 and the closest to this axis, into collecting zones 6.4a which are connected to a central collecting zone 6.5a from which said fluid is then drawn off.

The apparatus used in the second type of flow of the thermoregulation fluid further comprises (see FIG. 2):

(a) at least one central distributing collector 6.1b, for example vertical, whose axis generally corresponds to the axis of the enclosure 1, which is situated above a central receiving collector 6.5b defined below and which is connected to duct 2, (b) a plurality of connecting collectors 6.6b parallel to the axis of the enclosure, (c) at least one central receiving collector 6.5b, for example vertical, whose axis corresponds generally to the axis of the enclosure, which is situated below the central distributing collector 6.1b and which is connected to duct 3, (d) a plurality of hollow continuous and elongate plates (or hollow internal spaces) 6.3b intended for the flow of the thermoregulation fluid, said plates being associated two by two, each association comprising two series of plates, a first series of plates 6.3, 1b being situated above the second series, each of the plates of the first series 6.3, 1b being open on to a connecting collector 6.6b and on to the central distributing collector 6.1b, a second series of plates 6.3, 2b being situated below the first series of plates 6.3, 1b, each of the plates of this second series 6.3, 2b being situated in the extension of a plate of the first series 6.3, 1b (the plates of the first series not being adjacent those of the second series), being open on to a connecting collector 6.6b which causes each plate of this second series to communicate with a plate of the first series situated in its extension, and being open on to the central receiving collector 6.5b.

According to an improvement, the faces of said hollow plates may be formed by corrugated metal sheets whose corrugations are chosen from one of the following forms: square, rectangular, triangular, sinusoidal and a herring bone pattern (see FIG. 4D), the aim being also to create a high turbulence in the flow of the thermoregulation fluid.

In the apparatus used in the second type of thermoregulation fluid flow, said hollow plates are substantially parallelepipedic, each plate comprising two wide parallel faces defining a plane disposed radially with respect to the axis of the enclosure 1 and four thin faces, two of them being parallel to the axis of the enclosure, the other two being perpendicular to this axis. Said plates are associated two by two, each association comprising two series of plates, a first series of plates 6.3,1b being situated above the second series 6.3,2b. Each of the plates of this first series 6.3,1b is open, over the whole of its thin face parallel to the axis of the enclosure and the furthest away from this axis, on to a connecting collector 6.6b and open, over the whole of its thin face parallel to the axis of the enclosure and the closest to this axis, on to the central distributing collector 6.1b. The second series of plates 6.3,2b is situated below the first series of plates 6.3,1b, each of the plates of this second series 6.3,2b being situated in the extension of a plate of the first series 6.3,1b (the plates of the first series not being adjacent those of the second series); each of the plates of the second series 6.3,2b is open, on the one hand, over the whole of its thin face parallel to the axis of the enclosure 1 and the furthest away from this axis, on to a connecting collector 6.6b which causes each plate of this second series to communicate with a plate of the first series situated in its extension and, on the other hand, over the whole of its thin face parallel to the axis of the enclosure and the closest to this axis, on to the central receiving collector 6.5b. Said thin faces of each hollow plate may possibly be not flat, but for example semi-cylindrical.

In FIG. 2, given by way of example, the path of the thermoregulation fluid through the hollow plates (hollow internal spaces) which are substantially parallelepipedic (contained in the reaction zone 1) will be described:

the thermoregulation fluid (autogenous) is fed into a central distribution zone 6.1b, said fluid is caused to penetrate, from said central distribution zone 6.1b, into a first series of hollow internal spaces 6.3,1b, defined by walls and of a substantially parallelepipedic shape (each parallelepipedic space of the first series thus comprising two parallel wide faces defining a plane disposed radially with respect to the axis of the reaction zone 1 and four thin faces, two of them being parallel to the axis of the reaction zone 1, the other two being perpendicular to this axis), said fluid penetrating into said hollow internal spaces of the first series 6.3,1b through their thin face parallel to the axis of the reaction zone 1 and the closest to this axis, said fluid is caused to flow inside said upper hollow internal spaces of the first series 6.3,1b in the form of a sheet, said fluid is discharged from said hollow internal spaces of the first series 6.3,1b, through their thin face parallel to the axis of the reaction zone 1 and the furthest away from this axis, into connecting zones 6.6b which each cause a hollow internal space of the first series 6.3,1b to communicate with a hollow internal space of a second series 6.3,2b situated in its extension, each space of the second series 6.3,2b being defined by walls and having a substantially parallelepipedic shape which is defined as for a space of the first series 6.3,1b, said fluid is caused to penetrate, from said connecting zones 6.6b, into said hollow internal spaces of the second series 6.3,2b, through their thin face parallel to the axis of the reaction zone 1 and the furthest from this axis, said fluid is caused to flow inside said hollow internal spaces of the second series 6.3,2b in the form of a sheet, said thermoregulation fluid is discharged from said hollow internal spaces of the second series 6.3,2b, through their thin face parallel to the axis of the reaction zone 1 and the closest to this axis, into a central collecting zone 6.5b from which said fluid is then drawn off.

According to an improvement, the apparatus of the second type may contain several associations of two series of plates (or internal spaces), said associations being stacked along the axis of the enclosure (see FIG. 3). In FIG. 3, two associations having two series of plates each have been shown arbitrarily, but the number of such associations may be higher; in FIG. 3, the thermoregulation fluid follows the path shown by arrows F, gradually through two associations of two series of plates; this fluid may thus successively travel twice over the path shown in FIG. 2. When the number of associations of two series of plates is equal to n, with n greater than 2, then the thermoregulation fluid travels successively n times over the path shown in FIG. 2.

The advantage of an autogenous thermoregulation fluid is, on the one hand, that there is no pressure difference between the inside and the outside of the plates (apart from that created by the pressure losses due to the flow of the different fluids) and, on the other hand, that, in the case of a leak, there is no danger of pollution of the catalytic system.

In a variant of the invention, said hollow plates may if required have different lengths, which makes it possible to maintain a minimum ratio between the volume of the enclosure and the exchange area, while avoiding too great a distance between any point of the enclosure and the nearest plate.

It should be noted that adjacent channels may be formed in substantially parallelepipedic hollow plates (see FIGS. 4A, 4B and 4C) by means of corrugated metal sheets, the sections of said channels being chosen from one of the following forms: square, rectangular (7A), triangular (7B) and sinusoidal (7C), these channels connecting together the two thin faces parallel to the axis of the enclosure of the same plate: on the one hand, the presence of these adjacent channels ensures the strength of the hollow plates which may reach and exceed for example 10 meters in height and, on the other hand, it avoids the formation of dead zones (i.e. zones through which the thermoregulation fluid does not flow) which might be formed because of the sheet flow of the thermoregulation fluid inside the plates.

The metal sheets may be assembled together by welding, or much more economically by brazing, either by points or by immersion into a bath, or any other adequate technique.

The metal sheets possibly used in the different embodiments of the invention generally have a thickness less than 10 mm, preferably less than 3 mm.

In the figures, enclosure 1 is shown in a substantially vertical position: the flow of the thermoregulation fluid and of the make-up charge may take place from top to bottom, as described above, but also from bottom to top (and so also contraflow wise).

Each of the FIGS. 1, 2 and 3 shows an axial reactor (enclosure) in which the reagents pass through the catalyst bed parallel to the axis of the reactor.

The invention may be applied to a radial reactor comprising a permeable basket in the form of a cylindrical ring, for example defined by two coaxial cylinders, in which the catalyst and the hollow plates are disposed and where the reagents pass through the bed perpendicularly to the axis of the reactor.

EXAMPLE 1 (according to the invention)

In a vertical cylindrical reactor, 0.5 m in diameter, equipped with a hollow plate thermoregulation system in accordance with FIGS. 1 and 4A, a catalyst is disposed obtained by depositing 3.5% by weight of sodium on potassium carbonate flakes bonded by 1.5% of graphite and previously activated at 230° C. for 3 hours.

Then, the unit shown in FIG. 5 is filled under a pressure of 9 MPa (through duct 8) with propane and a recirculation of 300 m$^3$/h is provided by means of a pump 13.

By means of the external steam heater 15, the temperature of the propane is progressively raised. When this temperature reaches about 150° C., polypropylene is introduced into the unit (through duct 8), while draining the propane off through duct 16.

After a few hours, stationary state is established with a propylene flowrate of 5 m$^3$/h, 28.9% conversion of propylene and a methyl-4 pentene-1 selectivity of 89.8%.

This state was able to be maintained for several hundred hours without substantial variation of the conversion of propylene and the methyl-4 pentene-1 selectivity.

EXAMPLE 2 (according to the invention)

The same operating conditions are used as in example 1, with the hollow plate thermoregulation system being in accordance with FIGS. 2 and 4C.

After a few hours of operation, stationary STATE is established with a propylene flowrate of 5 m$^3$/h, a conversion of propylene of 29.1% and a methyl-4 pentene-1 selectivity of 89.7%. This state was able to be maintained for several hundred hours without a substantial variation of this conversion and this selectivity.

EXAMPLE 3 (comparative)

The same catalyst is used as in example 1, which is disposed in the same reactor from which the thermoregulation system of the invention has been removed, the hourly flowrate of propylene being identical.

The temperature of the propylene supplied to the reactor is 180° C. The temperature of the reaction effluent leaving the reactor is 190° C.

It will be noted that the conversion of the propylene does not exceed 15.0% and the methyl-4 pentene-1 selectivity only reaches 65.1%, the major part of the by-products of the reaction being formed by methyl-4 pentene-2.

It will be observed in addition that after 50 hours or so the catalyst lost a great part of its activity.

What is claimed is:

1. A catalytic method for dimerizing or codimerizing or oligomerizing olefins, carried out under pressure, in the presence of a solid catalyst, in a reaction zone defined by a substantially cylindrical enclosure whose section is substantially circular, said enclosure containing a catalyst bed in which a plurality of hollow internal spaces is disposed, through which flows a thermoregulation fluid, at a pressure substantially equal to the pressure to which the reaction mixture is subjected, each hollow internal space being divided in the width direction into an upper hollow internal semi-space and a lower hollow internal semi-space, in which method:

a fresh liquid charge containing at least one olefin, mixed with a recycled charge defined below, is introduced into said hollow internal spaces defined by walls, the weight ratio between the recycled charge and the fresh charge being between 1 and 500, the fresh charge-recycled charge mixture forming the thermoregulation fluid;

the thermoregulation fluid is drawn off from said internal spaces and this fluid is separated into two portions called hereafter recycled charge and make-up charge, the weight ratio between said recycled charge and said make-up charge being between 1 and 500;

said recycled charge is fed into said hollow internal spaces as thermoregulation fluid component;

said make-up charge is fed into said catalyst bed;

a reaction effluent is drawn off from said catalyst bed, in which method in addition:

the thermoregulation fluid is fed into a central distributing zone, said fluid from the central distributing zone is divided up into distributing zones, said fluid is caused to penetrate from said distributing zones into said upper hollow internal semi-spaces, defined by walls, each upper semi-space having a substantially parallelepipedic shape, said fluid penetrating into said hollow upper internal semi-spaces through their thin face parallel to the axis of the reaction zone and the closest to this axis, said fluid is caused to flow inside said upper hollow internal semi-spaces in the form of a sheet, said fluid is discharged, from said upper semi-spaces, through their thin face parallel to the axis of the reaction zone and the furthest away from this axis, into connecting zones which each connect an upper semi-space with a lower hollow internal semi-space situated in the extension of said upper semi-space, each lower semi-space being defined by walls and having a substantially parallelepipedic shape, said fluid is caused to penetrate, from said connecting zones, into said lower hollow internal semi-spaces, through their thin face parallel to the axis of the reaction zone and the furthest from this axis, said fluid is caused to flow inside said lower hollow internal semi-space in the form of a sheet, said thermoregulation fluid is discharged, from said lower semi-spaces, through their thin face parallel to the axis of the reaction zone and the closest to this axis, into collecting zones which are connected to a central collecting zone from which said fluid is then drawn off.

2. A catalytic method for dimerizing or codimerizing or oligomerizing olefins, carried out under pressure, in the presence of a solid catalyst, in a reaction zone defined by a substantially cylindrical enclosure whose section is substantially circular, said enclosure containing a catalyst bed in which a plurality of hollow internal spaces is disclosed, through which flows a thermoregulation fluid, at a pressure substantially equal to the pressure to which the reaction mixture is subjected, in which method:

a fresh liquid charge containing at least one olefin, mixed with a recycled charge defined below, is introduced into said hollow internal spaces defined by walls, the weight ratio between the recycled charge and the fresh charge being between 1 and 500, the fresh charge-recycled charge mixture forming the thermoregulation fluid;

the thermoregulation fluid is drawn off from said internal spaces and this fluid is separated into two portions called hereafter recycled charge and make-up charge, the weight ratio between said recycled charge and said make-up charge being between 1 and 500;

said recycled charge is fed into said hollow internal spaces as thermoregulation fluid component;

said make-up charge is fed into said catalyst bed;

a reaction effluent is drawn off from said catalyst bed, in which method in addition:

the thermoregulation fluid is fed into a central distributing zone, said fluid is caused to penetrate, from said central distributing zone, into a first series of hollow internal spaces defined by walls and of a substantially parallelepipedic shape, said fluid penetrating into said hollow internal spaces of the first series through their thin face parallel to the axis of the reaction zone and the closest to this axis, said fluid is caused to flow inside said upper hollow internal spaces of the first series in the form of a sheet, said fluid is discharged, from said hollow internal spaces of the first series, through their thin face parallel to the axis of the reaction zone and the furthest away from this axis, into connecting zones which each cause a hollow internal space of the first series to communicate with a hollow internal space of a second series situated in its extension, each space of the second series being defined by walls and having a substantially parallelepipedic shape, said fluid is caused to penetrate, from said connecting zones, into said hollow internal spaces of the second series through their thin face parallel to the axis of the reaction zone and the furthest from this axis, said fluid is caused to flow inside said hollow internal spaces of the second series in the form of a sheet, said thermoregulation fluid is discharged, from said hollow internal spaces of the second series, through their thin face parallel to the axis of the reaction zone and the closest to this axis, into a central collecting zone from which said fluid is then drawn off.

3. A method according to claim 2 wherein several associations of two series of hollow internal spaces are used, said associations being stacked along the axis of the reaction zone.

4. A method according to claim 1 wherein the fresh charge is pre-heated by indirect contact with the reaction effluent.

5. A method according to claim 1 wherein the weight ratio between said recycled charge and said fresh charge is between 2 and 200.

6. A method according to claim 1 wherein the weight ratio between said recycled charge and said make-up charge is between 2 and 200.

7. A method according to claim 1 applied to the selective dimerization of propylene into methyl-4 pentene-1.

8. A method according to claim 2, wherein the fresh charge is pre-heated by indirect contact with the reaction effluent.

9. A method according to claim 2, wherein the weight ratio between said recycled charge and said fresh charge is between 2 and 200.

10. A method according to claim 2, wherein the weight ratio between said recycled charge and said make-up charge is between 2 and 200.

11. A method according to claim 2, applied in the selective dimerization of propylene into methyl-4 pentene-1.

12. A method according to claim 8, wherein several associations of two series of hollow internal spaces are used, said associations being stacked along the axis of the reaction zone.

13. A method according to claim 9, wherein several associations of two series of hollow internal spaces are used, said associations being stacked along the axis of the reaction zone.

14. A method according to claim 10, wherein several associations of two series of hollow internal spaces are used, said associations being stacked along the axis of the reaction zone.

15. A method according to claim 11, wherein several associations of two series of hollow internal spaces are used, said associations being stacked along the axis of the reaction zone.

* * * * *